(12) United States Patent
Lafont et al.

(10) Patent No.: US 10,314,804 B2
(45) Date of Patent: Jun. 11, 2019

(54) COMPOSITION CONTAINING NORBIXIN FOR PROTECTING CELLS OF THE RETINAL PIGMENT EPITHELIUM

(71) Applicants: BIOPHYTIS, Paris (FR); UNIVERSITE PARIS 6 PIERRE ET MARIE CURIE, Paris (FR)

(72) Inventors: René Lafont, Paris (FR); Stanislas Veillet, Savigny-sur-Orge (FR); José-Alain Sahel, Paris (FR); Valérie Fontaine, Paris (FR); Pierre-Paul Elena, Nice (FR)

(73) Assignees: BIOPHYTIS, Paris (FR); SORBONNE UNVERSITÉ, Paris (FR)

( * ) Notice: Subject to any disclaimer, the term of this patent is extended or adjusted under 35 U.S.C. 154(b) by 0 days.

(21) Appl. No.: 15/570,720

(22) PCT Filed: Apr. 28, 2016

(86) PCT No.: PCT/FR2016/051001
§ 371 (c)(1),
(2) Date: Oct. 30, 2017

(87) PCT Pub. No.: WO2016/174360
PCT Pub. Date: Nov. 3, 2016

(65) Prior Publication Data
US 2018/0289651 A1 Oct. 11, 2018

(30) Foreign Application Priority Data

Apr. 30, 2015 (FR) ..................... 15 53957

(51) Int. Cl.
| | | |
|---|---|---|
| *A61K 33/30* | (2006.01) | |
| *A61P 27/02* | (2006.01) | |
| *A23L 33/105* | (2016.01) | |
| *A61K 31/202* | (2006.01) | |
| *A61K 31/355* | (2006.01) | |
| *A61K 31/375* | (2006.01) | |
| *A61K 36/185* | (2006.01) | |

(52) U.S. Cl.
CPC .......... *A61K 31/202* (2013.01); *A23L 33/105* (2016.08); *A61K 31/355* (2013.01); *A61K 31/375* (2013.01); *A61K 33/30* (2013.01); *A61K 36/185* (2013.01); *A61P 27/02* (2018.01); *A23V 2002/00* (2013.01)

(58) Field of Classification Search
None
See application file for complete search history.

(56) References Cited

U.S. PATENT DOCUMENTS

| | | |
|---|---|---|
| 9,173,823 B2 | 11/2015 | Veillet et al. |
| 2012/0149776 A1 | 6/2012 | Veillet et al. |
| 2014/0322371 A1 | 10/2014 | Veillet et al. |

FOREIGN PATENT DOCUMENTS

| | | |
|---|---|---|
| FR | 2 947 173 A1 | 12/2010 |
| FR | 2 975 008 A1 | 11/2012 |
| JP | 2010 285364 A | 12/2010 |
| WO | 01/85183 A2 | 11/2001 |
| WO | 2005/110375 A1 | 11/2005 |
| WO | 2010/149942 A1 | 12/2010 |

OTHER PUBLICATIONS

U.S. Appl. No. 14/117,461, dated Mar. 2014, Veillet; Stanislas, A61K31/161, 424/776.*
U.S. Appl. No. 15/688,917, dated Aug. 2017, Veillet; Stanislas, A61K31/191.*
Areds Report No. 8. 2001, "A randomized, placebo-controlled, clinical trial of high-dose supplementation with vitamins C and E, beta carotene, and zinc for age-related macular degeneration and vision loss," Arch Ophthalmol., Oct. 2001, vol. 119, No. 10, pp. 1417-1436.
Asai et al., "Orally administered crocetin and crocins are absorbed into blood plasma as crocetin and its glucuronide conjugates in mice," J. Agric. Food Chem., 2005, vol. 53, No. 19, pp. 7302-7306.
Bhosale et al, "Retinal carotenoids can attenuate formation of A2E in the retinal pigment epithelium," Arch. Biochem. Biophys., 2009, vol. 483, pp. 175 181.
Bisti et al., "Saffron and retina: neuroprotection and pharmacokinetics," Visual Neurosci., May 12, 2014, vol. 31, pp. 335-361.
Chabera et al., "Effect of carotenoid structure on excited-state dynamics of carbonyl carotenoids," Phys. Chem. Chem. Phys., Jul. 31, 2009, vol. 11, pp. 8795-8803.
Elliot et al., "Nutrients in the battle against age-related eye diseases," American Optometric Association, 2012, pp. 47-55.
Falsini et al., "Influence of saffron supplementation on retinal flicker sensitivity in early age-related macular degeneration," IOVS, Dec. 2010, vol. 51, No. 12, pp. 6118-6124.
Fernandez-Sanchez et al., "Safranal, a saffron constituent, attenuates retinal degeneration in P23H rats," PLoS One, Aug. 2012, vol. 7, No. 9, pp. 1-11.
Goralczyk et al., "Occurrence of birefringent retinal inclusions in cynomolgus monkeys after high doses of canthaxanthin," Invest. Ophthalmol. Vis. Sci., Mar. 1997, vool. 38, No. 3, pp. 741-752.
Hagiwara et al., "A thirteen-week oral toxicity study of annatto extract (norbixin), a natural food color extracted from the seed of annatto (Bixaorellana L.), in Sprague-Dawley rats," Food Chem. Toxicol., 2003, No. 41, pp. 1157-1164.
Laabich et al., "Protective effect of crocin against blue light- and white light-mediated photoreceptor cell death in bovine and primate retinal primary cell culture," Invest. Ophthalmol. Vis. Sci., Jul. 2006, vol. 47, No. 7, pp. 3156-3163.
Levy et al., "Bixin and norbixin in human plasma: Determination and study of the absorption of a single dose of annatto food color," Analyst, Sep. 1997, vol. 122, pp. 977-980.

(Continued)

*Primary Examiner* — Michael Barker
(74) *Attorney, Agent, or Firm* — Im IP Law; C. Andrew Im; Chai Im

(57) ABSTRACT

A method of photoprotecting cells of the retinal pigment epithelium (EPR) in mammals using a composition having norbixin. The norbixin is produced by purification from an extract of *Bixa orellana* seeds.

11 Claims, 13 Drawing Sheets

(56) References Cited

OTHER PUBLICATIONS

Liu et al., "Cis astaxanthin and especially 9-cisastaxanthin exhibits a higher antioxidant activity in vitro compared to the all-trans isomer," Biochem. Biophys. Res. Comm., Mar. 28, 2007, vol. 357, pp. 187-193.

Maccarone et al., "Saffron supplementation maintains morphology and function after exposure to damaging light in mammalian retina," Invest Ophthalmol. Vis. Sci., Mar. 2008, vol. 49, No. 3, pp. 1254-1261.

Maeda et al., "Retinopathy in mice induced by disrupted all-trans-retinal clearance," J. Biol. Chem., Sep. 26, 2008, vol. 283, No. 39, pp. 26684-26693.

Maeda et al., "Evaluation of potential therapies for a mouse model of human age-related macular degeneration caused by delayed all-trans-retinal clearance," Invest Ophthalmol. Vis. Sci., Oct. 2009, vol. 50, No. 10, pp. 4917-1925.

Melendez-Martinez et al., "A simple HPLC method for the comprehensive analysis of cis/trans (Z/E) geometrical isomers of carotenoids for nutritional studies," Food Chem., 2013, vol. 138, pp. 1341-1350.

Montenegro et al., "Model studies on the photosensitized isomerization of bixin," J. Agric. Food Chem., 2004, vol. 52, pp. 367-373.

Parisi et al., "Carotenoids and antioxidants in age-related maculopathy Italian study: multifocal electroretinogram modifications after 1 year," Ophthalmology, Feb. 2008, vol. 115, No. 2, pp. 324-333.

Phan-Thi et al., "Isomerization and increase in the antioxidant properties of lycopene from Momordicacochinchinensis (gac) by moderate heat treatment with UV-Vis spectra as a marker," Food Chem., Jan. 23, 2014, vol. 156, pp. 58-63.

Pinazo-Duran et al., "Do nutritional supplements have a role in age macular degeneration prevention?," J. Ophthalmology, Jan. 23, 2014, vol. 2014, pp. 1-15.

Pintea et al., "Xanthophylls protect against induced oxidation in cultured human retinal pigment epithelial cells," J. Food Compos. Anal., Mar. 11, 2011, vol. 24, No. 6, pp. 830-836.

Rios et al., "Thermal degradation kinetics of bixin in an aqueous model system," J. Agric. Food Chem., Feb. 18, 2005, vol. 53, pp. 2307-2311.

Sparrow et al., "Blue light-induced apoptosis of A2E-containing RPE: involvement of caspase-3 and protection by Bcl-2," Invest Ophthalmol. Vis. Sci., May 2001, vol. 42, No. 6, pp. 1356-1362.

Subczynski et al., "Location of macular pigments in the most vulnerable regions of photoreceptor outer-segment membranes," Arch. Biochem. Biophys., Dec. 1, 2010, vol. 504, No. 1, pp. 61-66.

Tsuruma et al., "Annatto prevents retinal degeneration induced by endoplasmic reticulum stress in vitro and in vivo," Mol. Nutr. Food Res., 2012, vol. 56, pp. 713-724.

Verma et al., "Analysis of saffron (Crocus sativus L.) stigma components by LC-MS-MS," Chromatographia, Jan. 2010, vol. 71, pp. 117-123.

Widomska et al., "Why has nature chosen lutein and zeaxanthin to protect the retina?," J. Clin. Exp. Ophthalmol., May 30, 2014, vol. 5, No. 1, pp. 326-347.

Wu et al., "Light damage in Abca4 and Rpe65rd12 mice," Invest Ophthalmol. Vis. Sci., Mar. 2014, vol. 55, pp. 1910-1918.

Yamauchi et al., "Crocetin prevents retinal degeneration induced by oxidative stress and endoplasmic reticulum stress via inhibition of caspase activity," European J. Pharmacol., 2011, vol. 650, pp. 110-119.

Jang et al., "Anthocyanins protect against A2E photooxidation and membrane permeabilization in retinal pigment epithelial cells," Photochem Photobiol., 2005, vol. 81, No. 3, pp. 529-536.

\* cited by examiner

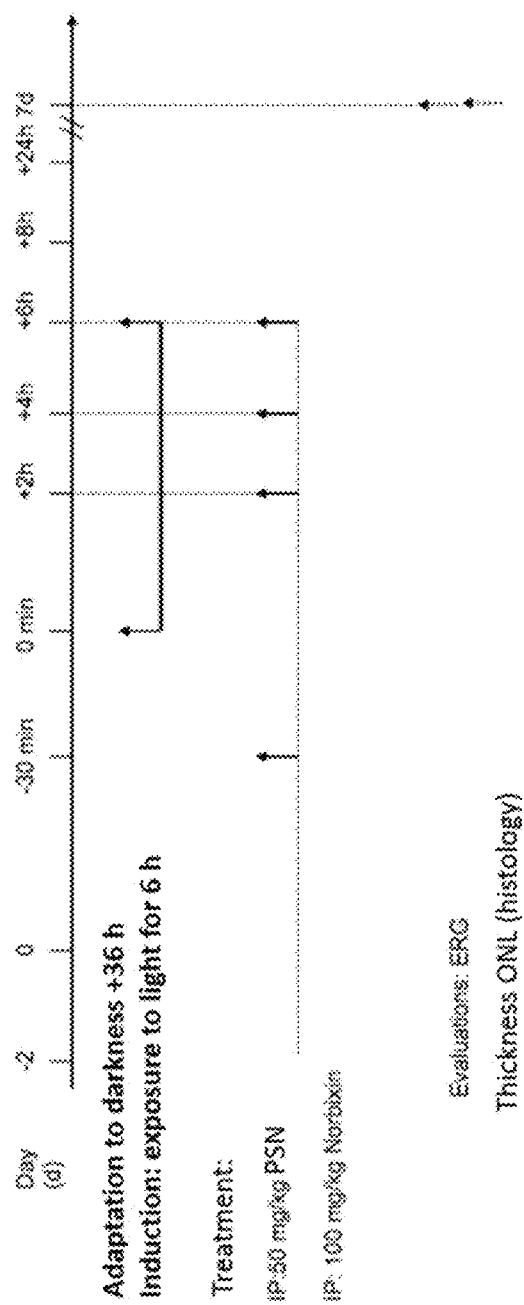

COMPOSITION CONTAINING NORBIXIN FOR PROTECTING CELLS OF THE RETINAL PIGMENT EPITHELIUM

RELATED APPLICATIONS

This application is a § 371 application from PCT/FR2016/051001 filed Apr. 28, 2016, which claims priority from French Patent Application No. 15 53957 filed Apr. 30, 2015, each of which is incorporated herein by reference in its entirety.

FIELD OF THE INVENTION

The present invention relates to the field of treatments of cells of the retinal pigment epithelium (RPE).

More particularly, the present invention targets the use of a composition for protecting the cells of the retinal pigment epithelium (RPE), in particular for treating age-related macular degeneration (ARMD) or else Stargardt disease and retinitis pigmentosa in mammals.

The objective of the invention is to improve the sight of individuals suffering from these diseases or at least to stabilize the progression of the disease.

BACKGROUND OF THE INVENTION

Age-related macular degeneration (ARMD) is a cause of irreversible blindness in elderly populations, in particular in Europe and in North America. ARMD affects the central part of the retina, called the macula, leading to a serious visual deficiency and the irreversible loss of central vision.

The macular function is responsible for central vision and visual acuity, the high resolution of which is linked to its high concentration of cone photoreceptors. The early stage of ARMD is marked by deposits called Drusen, which only marginally affect sight. The subsequent phases comprise two forms of ARMD, geographical atrophy (dry form) or exudative atrophy (wet or neovascular form), the first being much more common than the second. The final steps of these two forms result in the destruction of the macular neurosensory retina, but the progression of dry ARMD is generally slow, while wet ARMD can result in complete blindness in a few weeks.

Aging is the gradual accumulation over time of changes which are associated with (or responsible for) increasing susceptibility to the disease. In the retina, a certain number of degenerative diseases, including glaucoma, retinitis pigmentosa and ARMD, can occur following aging. Retinis pigmentosa groups together a heterogeneous set of genetic retinal degenerations, involving the photoreceptors and the RPE, and resulting in a loss of nocturnal vision, then later on of central vision. Although the specific mechanisms involved in the initiation of various types of diseases related to retinal aging differ, it is thought that the oxidative stress and the inflammation that result therefrom are important elements which contribute to the pathogenesis.

The theories about the etiology of ARMD include hydrodynamic modifications in Bruch's membrane caused by a gradual accumulation of extracellular material containing lipids, and senescence of the RPE, the activity of which is essential to the survival of the photoreceptors. The cells of the RPE have several different functions in the eyes: they establish the blood-retinal barrier through their tight junctions, and are thus responsible for the immunoprivileged status of the interior part of the eyeball; they keep the photoreceptors alive by providing them with nutrients and participate in the visual cycle. The current understanding is that a deficiency in the function of the cells of the RPE is responsible for the development of ARMD. The aging causes a dysfunction of the RPE cells and an insufficiency of their metabolism, and also of their phagocytic activity. Incomplete digestion of the external segments of the photoreceptors can result in the formation of Drusen by reducing the diffusion across the Bruch's membrane, which firstly causes a deformation of the retina and of the perceived images.

With age, the RPE stores an increasing amount of lipofuscins. These are composed of lipids and proteins, which originate from the phagolysosomes, lysosomes and photoreceptors. Lipofuscins also contain N-retinyl-N-retinylidene ethanolamine (A2E), which is formed by the condensation of two retinaldehyde molecules with ethanolamine.

Aging is accompanied by an increased accumulation of A2E in the retina (Bhosale et al., 2009). Under the action of blue light and in the presence of oxygen, A2E generates reactive species which cause damage to the proteins, to the lipids and to the DNA, and thus a significant oxidative stress in the aging cells of the RPE (Sparrow & Cai, 2001). This damage disrupts the lysosomal activity of cells of the RPE and causes an accumulation of waste, which ends up causing, from place to place, the death of cells of the RPE, which is followed by that of the photoreceptors with which they were associated.

No medicament exists on the market for the treatment of dry ARMD, whereas medicaments by intravitreal injection of anti-VEGF (Vascular Endothelial Growth Factor) antibodies are sold, making it possible to partially block the formation of neovessels and thus offering an alternative treatment for wet ARMD. Food supplements have been formulated with generic antioxidant compounds, namely minerals and vitamins with antioxidant properties, for example zinc, vitamins A, C, E, with an actual but limited therapeutic efficacy. The AREDS nutraceutical formula 1 ("*Age-Related Eye Disease Study*", AREDS 2001) is considered to be the standard for care in the United States for the treatment of dry ARMD, reducing the risk of advanced ARMD by 25% and sight loss by 19% over five years.

Numerous products propose a common formulation base: zinc and vitamins C and E, to which are added various ingredients: lutein, resveratrol, omega-3 fatty acids, without however providing convincing data about efficacy with regard to these additional ingredients, or with regard to the categories of patients who may respond favorably to these various molecules (Elliot & Williams, 2012). In particular, in the prior art, there is international application WO 2005/110375 which relates to a food supplement intended to limit them or prevent the loss of visual acuity of ocular after effects of a disease.

Carotenoids (molecules exclusively provided by the diet) have been more particularly studied, since some of them (lutein, zeaxanthin=xanthophylls) are naturally present in the macula (Subczynski et al., 2010), and it is known that these compounds have a strong anti-oxidizing power. It is thus logical for these compounds to have been tested (alone or in combination) in the AREDS formula, but the results obtained were limited, the supplementation proving to be efficacious only for a subset of patients with a deficiency in these compounds (Pinazo-Duran et al., 2014). These molecules are efficacious in vitro for protecting cells of the RPE (Human D407) against the toxic effects of hydrogen peroxide (Pintea et al., 2011).

Japanese patent application JP 2010285364 puts forward a mixture composed of crocetin and of another carotenoid that can be a xanthophyll or another diapocarotenoid, i.e. bixin or norbixin. This mixture, owing to its anti-oxidizing properties, is proposed for relieving or preventing diseases in which an oxidative phenomenon is involved.

Other xanthophylls have also been the subject of studies by oral supplementation, alone or in combination with lutein and/or zeaxanthin (for example astaxanthin—Parisi et al., 2008). Recently, diapocarotenoids (=carotenoids truncated at the two ends—IUPAC chemical nomenclature) have been tested in vitro and in vivo, in particular crocetin (=8,8'-diapocarotene-8,8'-dioate) and glycosides thereof (crocins). Crocins have an in vitro photoprotective effect on primary cultures of bovine or primate photoreceptors (Laabich et al., 2006), and crocetin protects neuroganglion cells against oxidative stress (Yamauchi et al., 2011). Saffron (a spice rich in crocins/crocetin) administered orally has proved to be active in vivo on the quality of the retina (Maccarone et al., 2008; Falsini et al., 2010; Boisti et al., 2014). However, since saffron contains other molecules that may be active on the retina, such as other carotenoids and also safranal formed at the same time as crocetin (Verma & Middha, 2010; Fernández-Sánchez et al., 2012), it is difficult to reach a conclusion with regard to the effect of crocetin alone.

Experiments have also been carried out with another apocarotenoid, bixin (=methylhydrogen 6,6'-diapocarotene-6,6'-dioate) or certain derivatives thereof, in vitro on neuroganglion cells and in vivo by intravitreal injections to counteract the effects of a stress of the endoplasmic reticulum (Tsuruma et al., 2012). The tests thus carried out most commonly evaluate an anti-oxidizing and thus protective activity of the compounds with respect to various cell types of the retina subjected to the presence of an oxidizing agent (for example hydrogen peroxide), and they are not therefore directly within the context of ARMD.

An extract of Urucum (Bixa orellana) seeds previously developed (Bixilia®) has shown a photoprotective effect on human skin exposed to UV radiation (FR 2947173, Veillet et al., 2009) and on RPE cells subjected to a photo-oxidizing stress (Fontaine et al., 2011). The Bixilia® extract is a natural extract of Urucum which has been enriched with bixin. Bixilia® contains other photoprotective compounds of phenolic nature, the presence of which might explain the greater photoprotective activity of the crude extract compared with bixin alone. In patent FR 11 54172 (Fontaine et al., 2011), the protective effect on RPE cells of some of the compounds of the Bixilia® extract is analyzed. The results of the tests using bixin or norbixin at the concentrations 0.1 micromolar (µM), 1 µM and 10 µM do not have any photoprotective activity and even imply that the higher the bixin or norbixin concentration, the less the RPE cells survive and therefore the weaker is the photoprotective effect. It is noted, inter alia, that substances such as cyanidin and ellagic acid at concentrations of 10 µM and 20 µM have an advantageous photoprotective effect on RPE cells.

A more thorough study has led to the active molecules present in the Bixilia® extract being identified and to their mechanism of action being specified, and then to their efficacy in vivo being demonstrated in mice and rats. This study has given rise to the present invention. The invention thus envisions finding a treatment for protecting RPE cells that is an alternative to those that already exist.

OBJECT AND SUMMARY OF THE INVENTION

The inventors have discovered that norbixin, in particular its 9'-cis form, makes it possible to strongly decrease the cell death caused by an illumination, with blue radiation, of the cells of the RPE pretreated with N-retinyl-N-retinylidene ethanolamine (A2E).

According to a first aspect, the present invention targets a composition comprising more than 90% by weight of norbixin obtained by purification from an extract of Bixa orellana seeds, for use thereof for photoprotecting the cells of the retinal pigment epithelium (RPE) in mammals.

In the context of the invention, the term "extract of Bixa orellana seeds" is intended to mean an extract prepared from the external part of the seeds, that is to say from the waxy substance covering the Bixa orellana seeds. This waxy substance is known to be rich in bixin and in other minor carotenoids, and also for its use as a food dye.

Norbixin, bioavailable in mammals after oral administration, is much better absorbed than bixin and is found in the eye, in particular in the retina.

In particular embodiments of the invention, the composition comprises more than 90% by weight of norbixin.

In particular embodiments of the invention, the composition comprises more than 95% by weight of norbixin.

In particular embodiments of the invention, the composition comprises more than 90% by weight of norbixin in its 9'-cis form of formula (I):

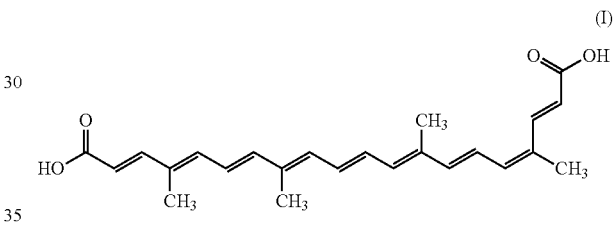

In particular embodiments, the composition comprises at least one element chosen from zinc, vitamin C and vitamin E.

In particular embodiments, the composition can be used in the form of a food supplement or of a medicament.

The term "food supplement" is intended to mean product containing said composition having the objective of supplementing the diet by providing nutrients that are beneficial to the health according to the definition given by European Directive 2002/46/EC. For example, a food supplement may be a gel capsule or tablet to be swallowed or a powder or small vial to be mixed with a food and which has beneficial effects on the RPE cells.

The term "medicament" is intended to mean product containing a precise dose of said compound or of said extract according to the definition given by European Directive 65/65/EC, namely any substance or composition presented as having curative or preventive properties with regard to human or animal diseases. For example, the medicament containing the compound at the therapeutic doses can be administered orally in the form of a gel capsule or tablet, or injected intravitreally or via any other route which makes it possible to confer beneficial effects on the retina.

In particular embodiments, the composition comprises a support acceptable for being ingested, injected in the eye, injected systemically or injected into the blood.

In embodiments, the composition is administered to the mammal, per day, in an amount of between 0.48 mg/kg of body weight and 48 mg/kg of body weight, preferably of between 0.6 mg/kg of body weight and 20 mg/kg of body weight.

According to other particular embodiments of the invention, the composition is intended for preventing damage to the retina that may be caused by exposure to blue radiation. The term "blue radiation" is intended to mean the radiation corresponding to the blue band of the visible light spectrum, having a wavelength of between 435 nm and 490 nm.

In particular embodiments of the invention, the composition is intended for the treatment of age-related macular degeneration (ARMD) in mammals.

In other particular embodiments, the composition is intended for treating Stargardt's disease and/or retinitis pigmentosa in mammals. Stargardt's disease, or Stargardt's syndrome, is a hereditary pathological condition, which combines a bilateral visual acuity decrease and atrophy of the macula, which reproduces, at an early age, the symptoms of the dry form of ARMD.

BRIEF DESCRIPTION OF THE FIGURES

FIG. 8A illustrates the experimental protocol of the creation of the "rat blue light" model.

DETAILED DESCRIPTION OF EXAMPLES OF IMPLEMENTATION OF THE INVENTION

Unlike most of the studies previously published, the models used in the present invention (both in vitro and in vivo) bring to the fore the role of N-retinyl-N-retinylidene ethanolamine (A2E) and of its phototoxicity, and in this respect are closer to the human pathological condition. The tests used in vitro are similar in terms of their principle to those used with other natural substances on a human RPE cell line (ARPE-19 cells—Young et al., 2005).

Protocols and Results

1—Preparation of Bixin and of Norbixin

Bixin which is 95% by weight pure is prepared from a commercial product (Annatto B) originating from an organic extraction of Urucum seeds and from a concentration of bixin greater than 85% by weight. The purification is carried out by successive recrystallizations.

Norbixin which is 95% by weight pure is obtained after alkaline hydrolysis of the purified bixin (5% KOH, 60° C., 3 hours). The solution obtained is acidified with concentrated hydrochloric acid and the norbixin is recovered by centrifugation. The pellet is washed twice with water in order to remove the salts, and the final pellet is lyophilized.

Figure 13:
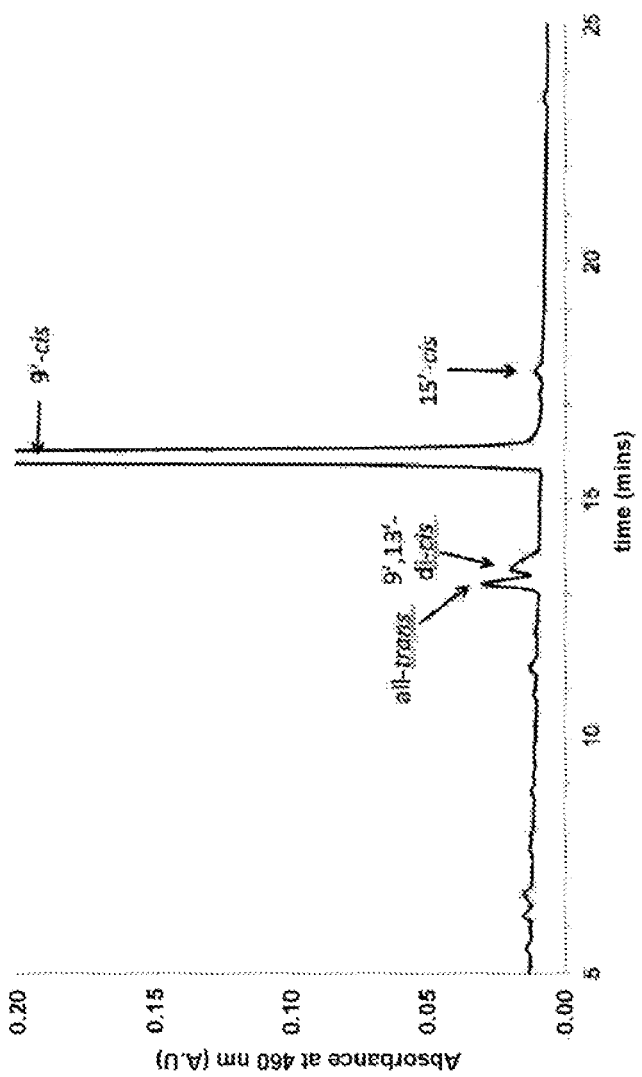
FIG. 13 illustrates the results of the reverse-phase HPLC analysis of norbixin purified from the extract of *Bixa orellana* (the isomers were identified according to Scotter et al., 1998 and Polar-Cabrera et al., 2010).

The purity of the compounds is assessed by UV-Vis spectrophotometry and reverse-phase HPLC: the compounds contain essentially the 9'-cis isomers (concentration greater than 90% by weight, FIG. 13).

2—In Vitro Tests

An in vitro test intended to study the photoprotective effect of various natural substances on the cells of the RPE placed in the presence of A2E was used. The photoprotective effect of the molecules is evaluated in a cell model of phototoxicity induced by treatment with A2E followed by an illumination with blue light. The term "blue radiation" is intended to mean the radiation corresponding to the blue band of the visible light spectrum, that is to say having a wavelength of between 435 and 490 nm.

This model uses primary cultures of adult pig RPE. The cell survival is quantified by means of a cell viability test. At −48 h, the compounds to be tested (in 5 mM solution in DMSO) are added so as to obtain final concentrations of 1 to 20 μM), then at −19 h, A2E is added (final concentration 30 μM) and the cells are irradiated (time 0 h). 24 h later, the cell survival is measured. The acquisition of the images and also the processing thereof are carried out by means of a fluorescence microscope controlled by the Metamorph software and of a dedicated quantification program. The experiments are carried out on 96-well microplates in quadruplicate and the experiment is reproduced a minimum of four times. The results are expressed in the form of a ratio representing the number of live cells in the wells treated with the molecules to be tested, divided by the number of live cells in the control wells (treated with the dilution medium without A2E).

This test previously made it possible to demonstrate the very good photoprotective activity of an ethanolic extract of Annatto seeds (Bixilia®—see Fontaine et al., 2011). In the previous work, while the activity of the extract of Annatto had been demonstrated, the nature of the photoprotective substance(s) had not been identified, and the main component of this extract (bixin) had proved to be ineffective at the concentrations of 0.1 µM, 1 µM and 10 µM. A supplementary work was thus undertaken in order to identify the active compound(s).

a. Bixin is Responsible for a Large Part of the Photoprotective Activity of Bixilia®

Figure 1:
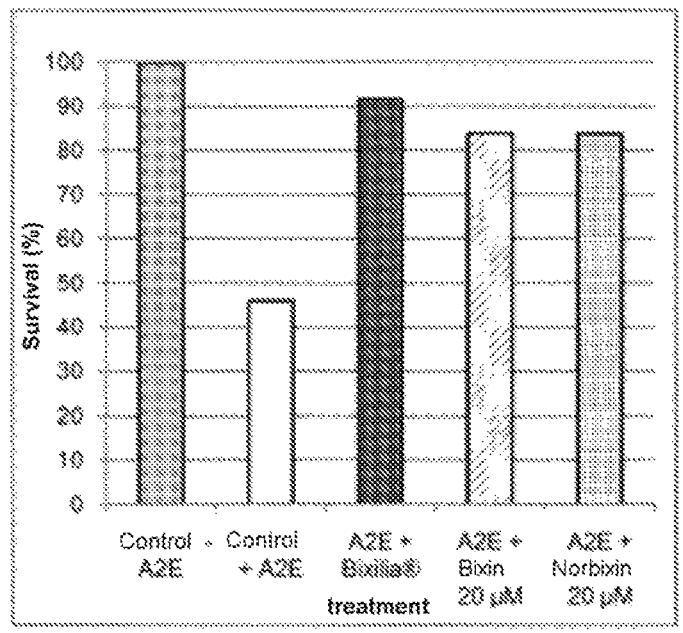
FIG. 1 illustrates the percentage of RPE cells surviving in the presence of N-retinyl-N-retinylidene ethanolamine (A2E) and of the Bixilia® extract or of bixin (20 μM) or of norbixin (20 μM) after having been subjected to an illumination.

FIG. 1 shows that bixin and norbixin (20 µM) effectively protect the cells of the RPE against the phototoxicity induced in the presence of A2E compared with the control with A2E. A crude extract of Urucum seeds, diluted to provide 20 µM of bixin, has a high photoprotective activity. The use of bixin which is very pure and at the concentration of 20 µM made it possible to show that this component in fact had a considerable photoprotective activity (FIG. 1) and that this explained a significant part of the activity of the Bixilia® extract diluted so as to give the same amount of bixin. A comparable activity was also found for norbixin, which represents the major circulating metabolite of bixin (Lévy et al., 1997). These results are in agreement with the photoprotective activity of these same compounds, previously demonstrated for the photoprotection of human skin (Veillet et al., 2009).

b. Bixilia® Contains Other Photoprotective Compounds

Bixilia® contains other photoprotective compounds of phenolic nature, the presence of which might explain the greater activity of the crude extract compared with bixin alone (for one and the same bixin concentration). A sequential extraction of the shell of the Urucum seeds was carried out with successively cyclohexane, dichloromethane and methanol (1 L of each/100 g of seeds).

After extraction with cyclohexane, a fraction with a bixin concentration of 0.65 µM is obtained; after extraction with dichloromethane, a fraction which has a bixin concentration of 1485 µM is obtained, and, after extraction with methanol, a fraction which has a bixin concentration of 45 µM is obtained.

The previous in vitro test is then reproduced.

Figure 2:
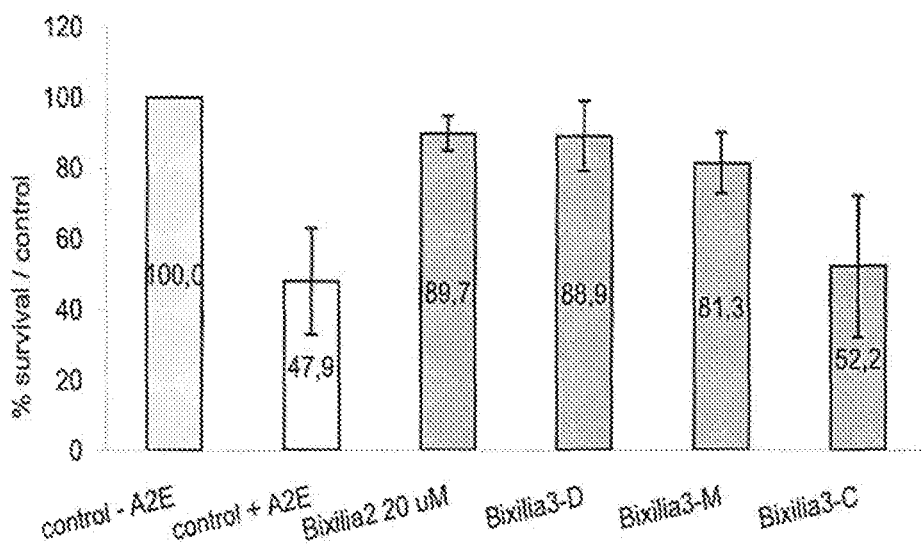
FIG. 2 illustrates the photoprotective activity of successive extracts of Urucum seeds (C=cyclohexane; D=dichloromethane; M=methanol) on the cells of the RPE placed in the presence of A2E and subjected to an illumination.

According to FIG. 2, the dichloromethane fraction, which contains 97% of bixin, is very active, but it is also noted that the methanolic extract rich in phenolic compounds has a significant activity (C=cyclohexane; D=dichloromethane; M=methanol).

3—Bioavailability of Bixin and of Norbixin

Figure 3A:
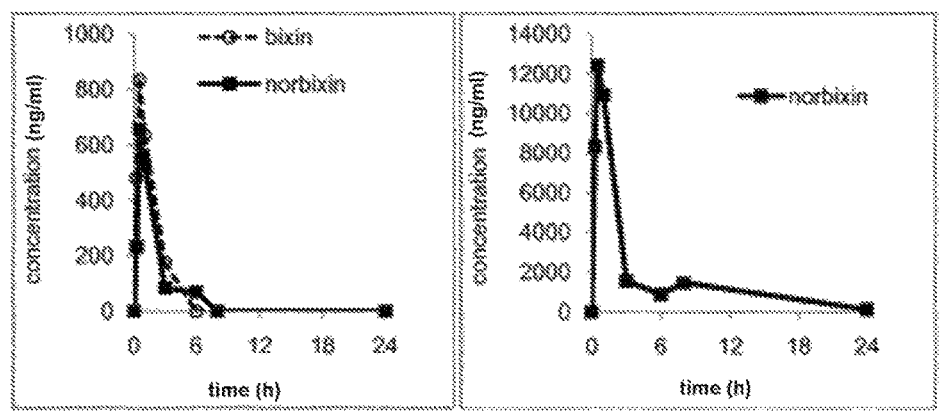
FIG. 3a illustrates the plasma concentrations after ingestion of bixin (on the left) or of norbixin (on the right) in C57Bl/6 mice.

Studies of the bioavailability of bixin and of norbixin were carried out in C57Bl/6 mice. The compounds were administered orally (50 mg/kg). Blood samples were taken after 0.25, 0.5, 1, 3, 6, 8 and 24 h and analyzed by HPLC-DAD (UV 460 nm)-MS/MS. Table 1 and FIG. 3a disclose that ingested bixin is rapidly converted into norbixin and that the two compounds circulate at comparable concentrations; they are no longer detected after 8 hours. It is also noted, moreover, that ingested norbixin is much more bioavailable than bixin.

TABLE 1

| | Bixin ingestion (50 mg/kg) | | | Norbixin ingestion (50 mg/kg) | |
|---|---|---|---|---|---|
| $T_{max}$ (h) | $C_{max}$ (ng/ml) | AUC 0-24 h (ng · h/ml) | $T_{max}$ (h) | $C_{max}$ (ng/ml) | AUC (ng · h/ml) |
| Bixin 0.5 | 833 | 1666 | Norbixin 0.5 | 12400 | 41609 |
| Norbixin 0.5 | 649 | 1343 | | | |

Figure 3B:
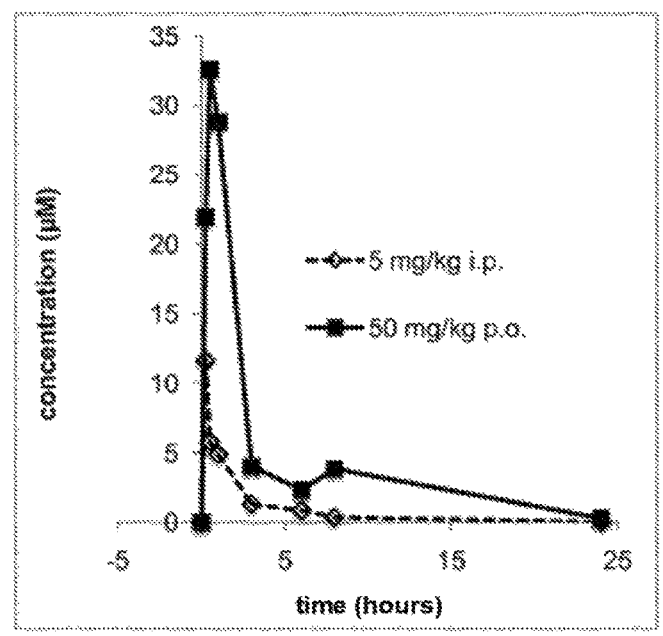
FIG. 3b illustrates the pharmacokinetic analysis of norbixin in C57Bl/6 mice.

The comparison of the plasma analyses (FIG. 3b) after intraperitoneal injection (5 mg/kg) and oral administration (50 mg/kg) shows that the bioavailability of norbixin is 55%.

The presence of norbixin in the eyes was investigated in double KO mice (ABCA4$^{-/-}$, RDH8$^{-/-}$) 3 hours after intraperitoneal injection of norbixin (10 mg/kg). The eyes of 6 animals were dissected and the samples were extracted with acetonitrile, pooled and then analyzed by HPLC-MS/MS (FIG. 4), which made it possible to specifically detect the presence of norbixin in the RPE and the retina (table 2).

TABLE 2

| Sample | Norbixin (ng/organ) |
|---|---|
| RPE | 5.15 |
| Retina | 2.40 |
| Crystalline | <LOQ |
| Vitreous humor | <LOQ |
| Total | 7.55 |

Figure 4:
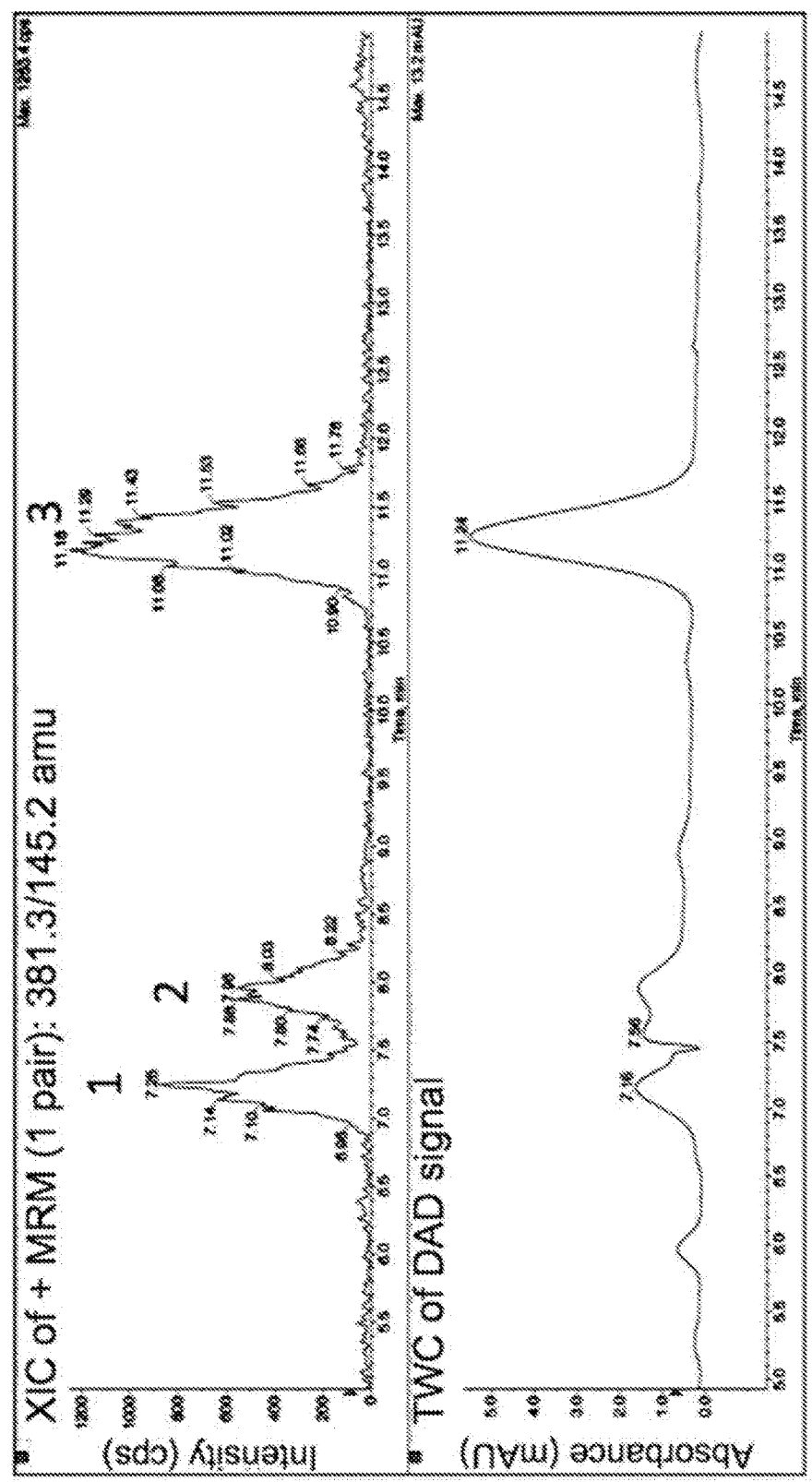
FIG. 4 illustrates the HPLC-MS/MS analysis of norbixin in the eyes of double KO mice (ABCA4$^{-/-}$, RDH8$^{-/-}$) after intraperitoneal injection (10 mg/kg). (3: injected norbixin, 1 and 2: monoglucuronides of this compound).

According to FIG. 4, it is noted that, in the plasma, but also in the eyes, the norbixin is also present in conjugated form: the initial compound in fact gives two monoglucuronides which are eluted before the original compound and exhibit a similar fragmentation, doubtless due to the decomposition of the glucuronides in the source of the mass spectrometer. Glucuronidation had also been described in the case of crocetin (Asai et al., 2005).

A cis-trans isomerization of the norbixin, the degree of which varies according to the duration of the experiments, can also be observed. It is a conventional phenomenon in (poly)unsaturated compounds, which corresponds to cis-trans isomerizations of one or more double bonds and has been observed in human beings in the case of norbixin by Lévy et al. (1997). The compound used herein is purified from commercial compounds (Annatto B); it very predominantly contains the 9-cis form and very small amounts of the all-trans form and of other cis or di-cis forms (FIG. 13).

4—Photoprotective Activity by Intravitreal Injection in Mice

Figure 5:
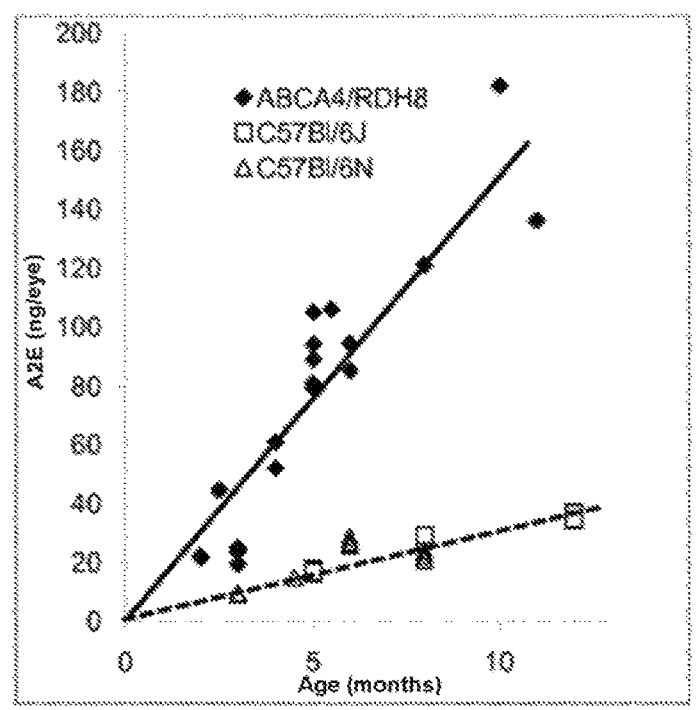
FIG. 5 illustrates the kinetics of A2E accumulation in the eye of double KO mice (ABCA4$^{-/-}$, RDH8$^{-/-}$) as a function of age, in comparison with normal mice.

A genetically modified mouse model developed by Maeda et al. (2008) was used to test the photoprotective activity of norbixin. In this mouse model, two genes involved in the visual pigment cycle (ABCA4 and RDH8) are inactivated, which results in an early accumulation of A2E in the eyes (FIG. 5). This animal model is as a result similar to the human pathological condition, with of course its limits, associated with the differences in organization of the eyes between rodents and primates.

Figure 6:
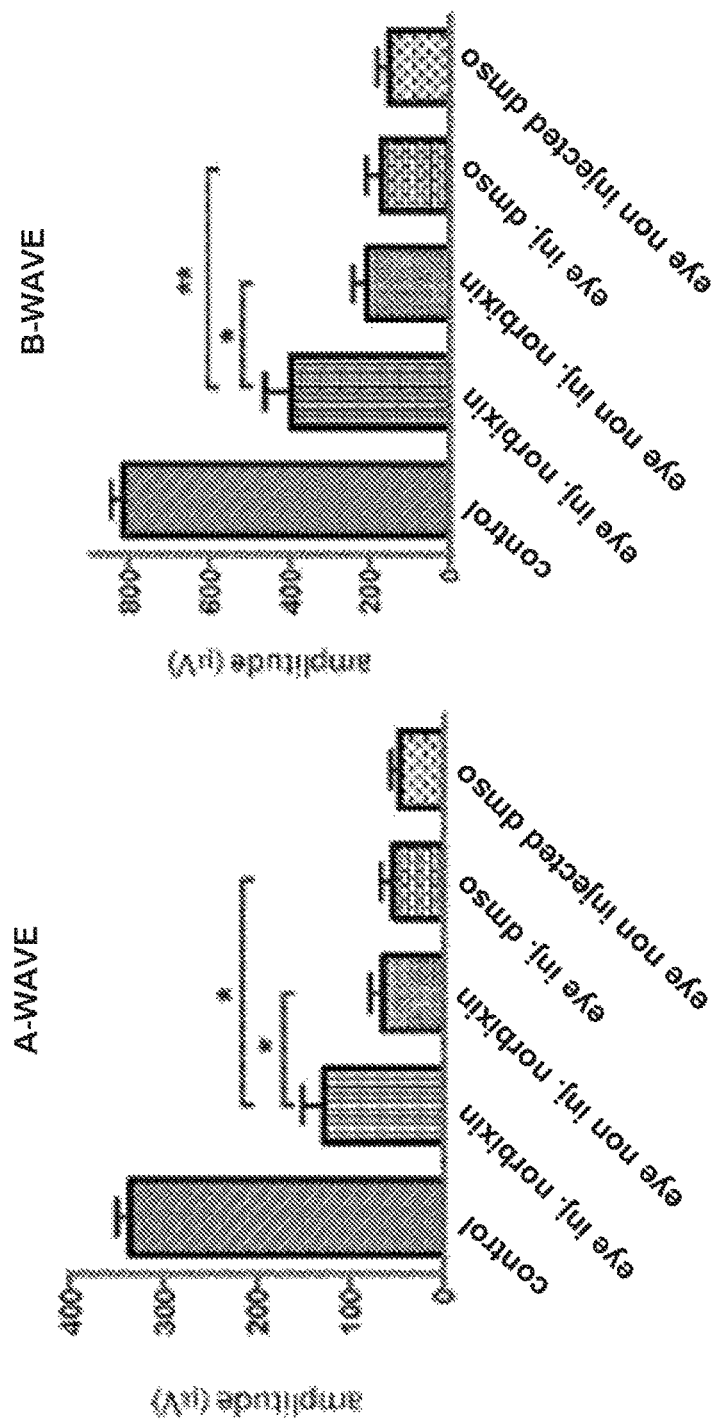
FIG. 6 illustrates the electroretinograms (A-waves on the left and B-waves on the right) of double KO mice (ABCA4$^{-/-}$, RDH8$^{-/-}$) having received unilateral intravitreal injections of norbixin (in order to obtain a final concentration in the vitreous body of 130 μM), placed in the dark for 24 h and then exposed to blue light (4000 lux, 1 h). The electroretinograms are carried out 7 days after the illumination.

7-week-old mice were thus used to carry out unilateral intravitreal injections of norbixin (in order to obtain a final concentration in the vitreous body of 130 µM). After 24 h in the dark, the mice were subjected to an exposure to blue light (4000 lux, 1 h). The electroretinograms carried out 7 days later showed a protective effect of norbixin, the presence of which made it possible to maintain a significant electric activity as shown by FIG. 6.

Figure 7:
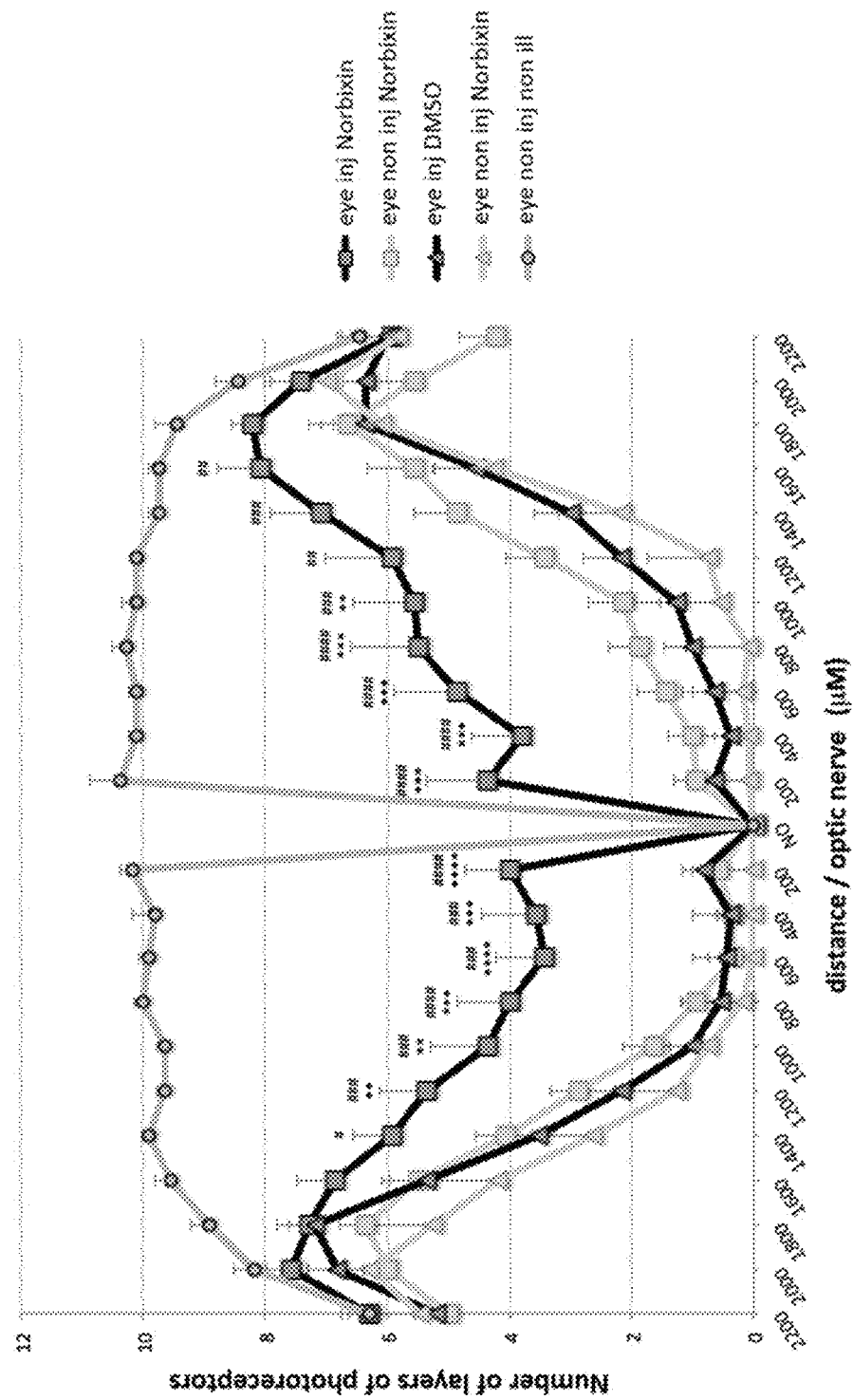
FIG. 7 illustrates the number of layers of photoreceptor nuclei as a function of the distance from the optic nerve in the eyes of mice treated as in FIG. 6.

A histological study of the thickness of the layer of external nuclei demonstrates the protective effect of norbixin on the photoreceptors (FIG. 7). It should be noted that the norbixin was virtually eliminated 24 h after the intravitreal injection and is therefore present only at very low levels in the eyes at the time of the illumination.

5—Photoprotective Activity by Systematic (Intraperitoneal) Injection in Rats

Figure 8B:
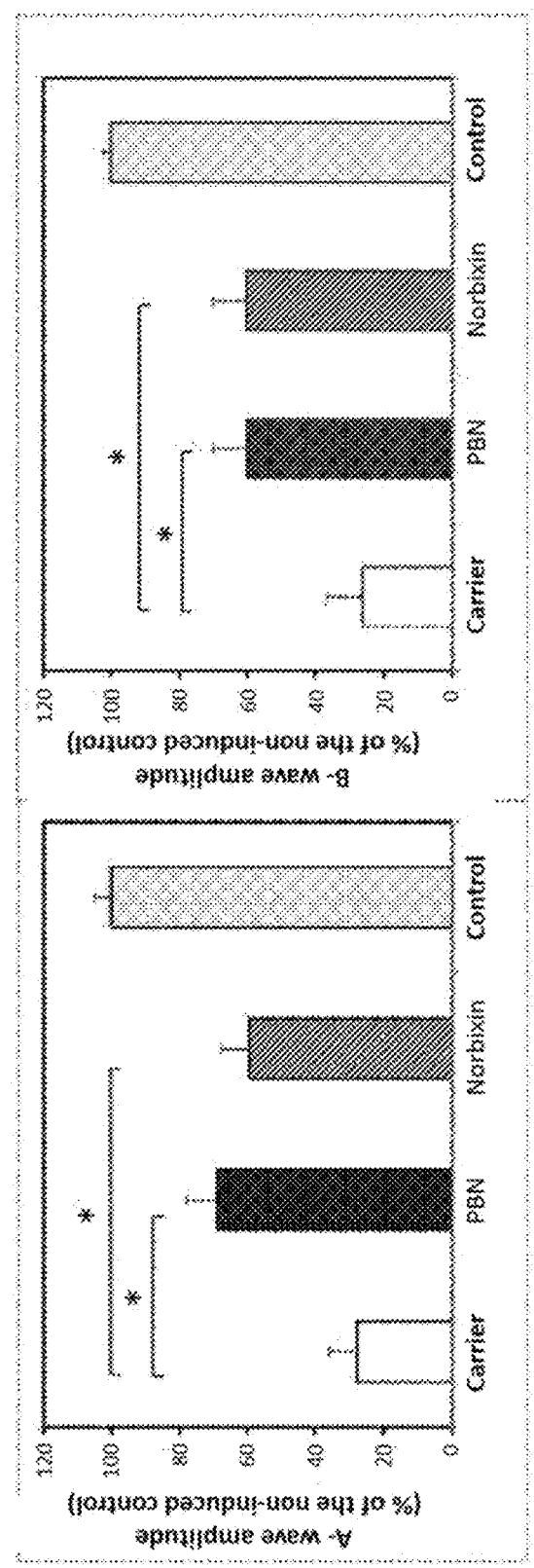
FIG. 8B illustrates the results of the electroretinograms of the rats which have been injected with norbixin (100 mg/kg, 4 injections per rat of a solution at 50 mM in 9‰ NaCl, 4 rats/series) using PBN (phenyl-N-tert-butylnitrone, 50 mg/kg, solution at 20 mg/ml in 9‰ NaCl) as positive control. The electroretinograms are carried out 7 days after the treatment.

The "rat blue light" model consists in subjecting the animals to a strong blue light for 6 hours in order to cause ocular damage that is assessed 7 days later by carrying out electroretinograms and then by histological analyses. An antioxidant compound, PBN (phenyl-N-tert-butylnitrone) is used as positive control (Ranchon et al., 2001; Tomita et al., 2005). The compounds of which it is sought to determine the photoprotective activity are injected (intraperitoneally) before and during the illumination phase. Said phase is carried out with Philips blue neon tubes (4.2 mW/cm$^2$) for 6 hours. The experimental protocol is presented in FIG. 8A.

Three series of experiments were carried out with norbixin (100 mg/kg, four injections per rat of a solution at 50 mM in 9‰ NaCl, 4 rats/series) using PBN (phenyl-N-tert-butylnitrone, 50 mg/kg, solution at 20 mg/ml in 9‰ NaCl) as positive control. The analysis of the electroretinograms (A-waves and B-waves) is presented in FIG. 8B.

Figure 9A:
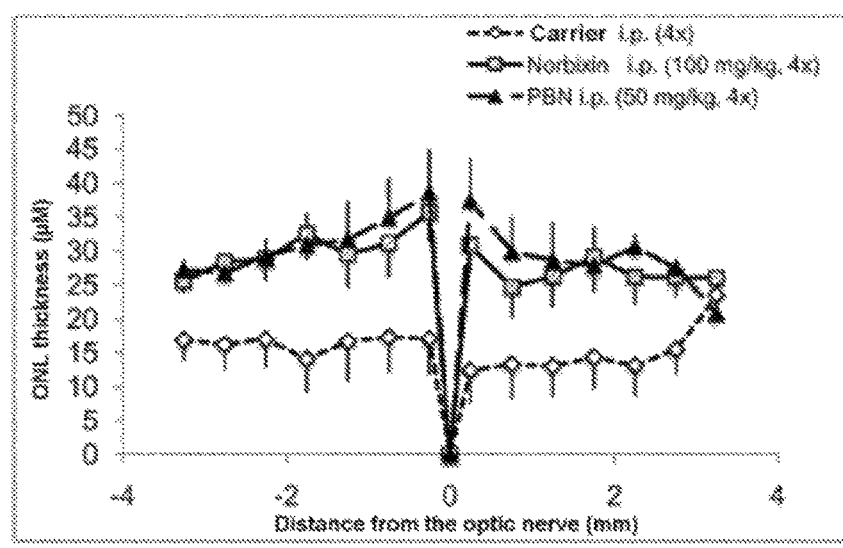
FIG. 9A illustrates the number of layers of photoreceptor nuclei as a function of the distance from the optic nerve in the eyes of rats after intraperitoneal injections of alpha-phenyl-N-tert-butylnitrone (PBN) or of norbixin and illumination with a blue light. The histological analyses are carried out 7 days after the treatment.
Figure 9B:
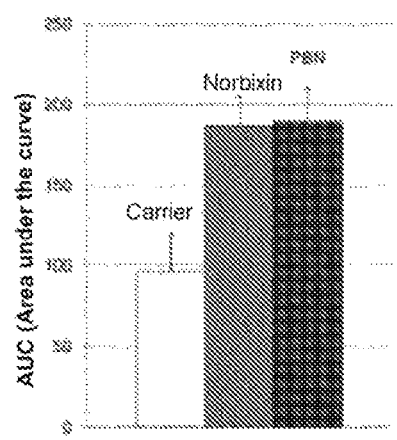
FIG. 9B illustrates the area under each curve of FIG. 9A.

This test made it possible to demonstrate a significant efficacity of norbixin, which is close to that of PBN. The corresponding histological data (FIGS. 9A and 9B) confirm the photoprotective action of norbixin on the survival of the photoreceptors.

6—Photoprotective Activity by Chronic Oral Administration in Mice

A feed containing 0.3 mg/g of pure norbixin was prepared and given to double KO mice (ABCA4$^{-/-}$, RDH8$^{-/-}$) for a period of 3 months.

Figure 10:
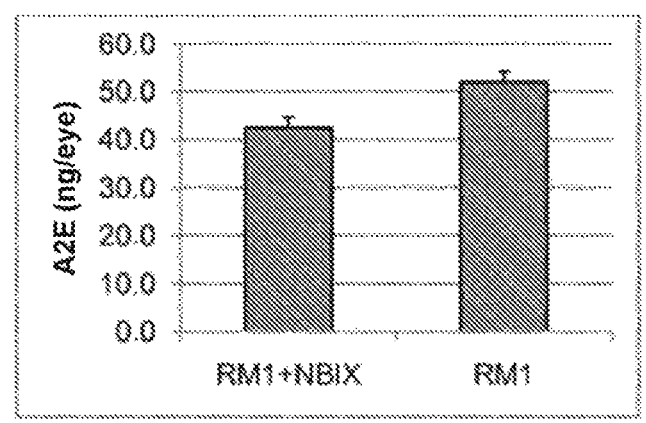
FIG. 10 illustrates the amount of A2E accumulated in the eye of double KO mice (ABCA4$^{-/-}$, RDH8$^{-/-}$) having ingested or not ingested feed supplemented with norbixin for 3 months.

The animals having received the feed supplemented with norbixin show a reduction in A2E accumulation in the eyes (FIG. 10): the difference between the two groups is very significant (p=0.0109).

Figure 11:
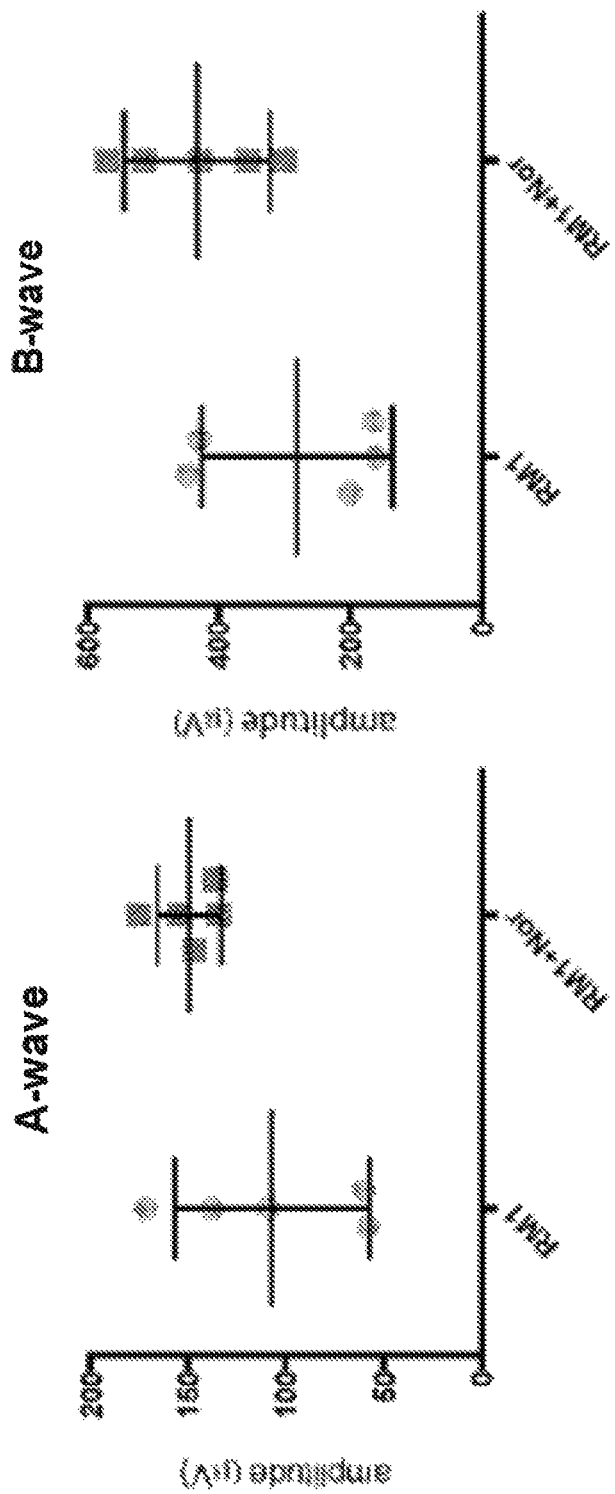
FIG. 11 illustrates the electroretinograms of double KO mice (ABCA4$^{-/-}$, RDH8$^{-/-}$) having been fed or not with feed containing 0.3 mg/g of pure norbixin for 3 months.

The feed supplemented with norbixin also has a positive effect on the amplitude of the electroretinogram (ERG) (FIG. 11).

Figure 12:
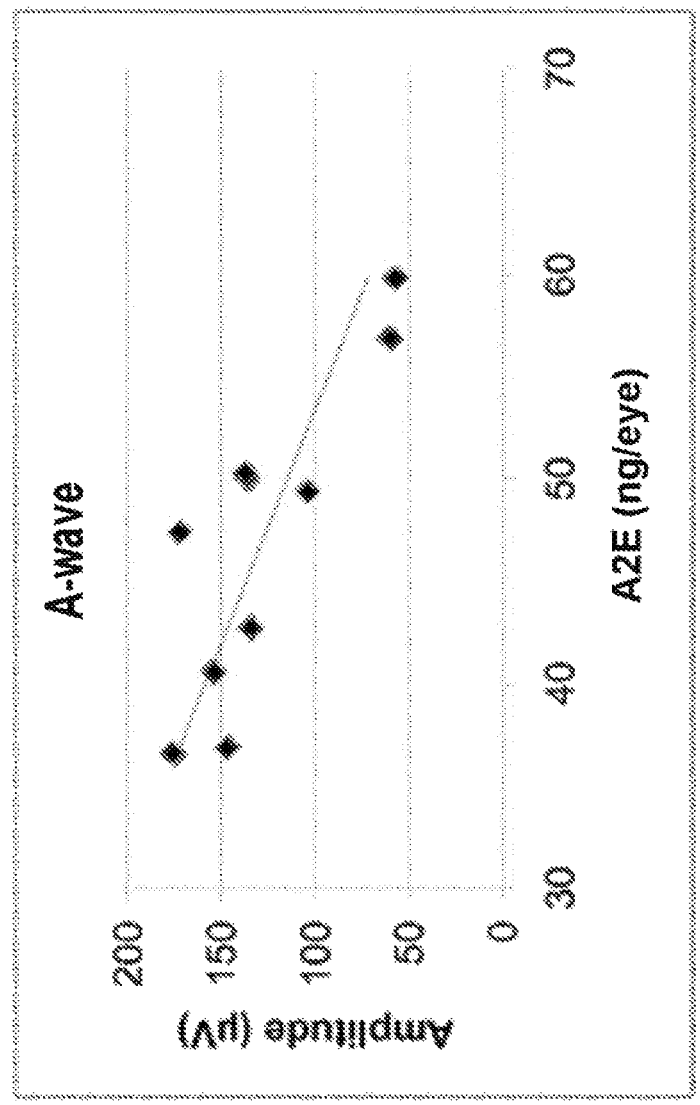
FIG. 12 illustrates the relationship between the amplitude of the electroretinogram (A-wave) and the amount of A2E accumulated in the eyes of the double KO mice (ABCA4$^{-/-}$, RDH8$^{-/-}$).

These analyses also showed that there is an inverse relationship between the amount of A2E accumulated in the eyes and the amplitude of the ERG (FIG. 12), which confirms the role of the A2E accumulation in the development of the pathological condition (Wu et al., 2014), and the advantage of molecules of which the administration reduces the A2E accumulation in the eyes.

However, no significant accumulation of norbixin is observed in the eyes during this chronic treatment, which leads to the conclusion that, unlike xanthophylls, this molecule appears to be degraded. The non-accumulation of this active substance can be considered to be an advantage, since the accumulation of some carotenoids (for example canthaxanthin) is capable of resulting in the formation of deposits within the cells of the RPE (Goralczyk et al., 1997). It is also an indication of an action modifying the activity of the cells of the RPE, rather than of a role of filter or of antioxidant, as postulated for lutein and zeaxanthin. This result is in agreement with that noted during the intravitreal injections (namely the disappearance of the norbixin at the time of the illumination).

The daily intake that makes it possible to significantly slow down the retinal degeneration in mice after oral administration is 48 mg/kg of body weight. Transposition to human beings results in proposing an active daily intake of 4.8 mg/kg. It is known, moreover, that the acceptable daily intake or ADI of norbixin is at most 0.6 mg/kg/day of body weight (JECFA/67/FC). This value was established on the base of an intake with no observable adverse effect level or NOAEL in rats of 69 mg/kg/day of body weight, equivalent to a daily intake with no observable adverse effect level in humans of 11 mg/kg, in the knowledge that no toxicity was observed up to 20 mg/kg/day (Hagiwara et al., 2003). The dosage regiment proposed is between 0.48 mg/kg/day and 48 mg/kg/day, ideally between 0.6 mg/kg/day and 20 mg/kg/day.

REFERENCES

AREDS Report No. 8. 2001. A randomized, placebo-controlled, clinical trial of high-dose supplementation with vitamins C and E, beta carotene, and zinc for age-related macular degeneration and vision loss. *Arch Ophthalmol*, 119: 1417-1436.

Asai A, Nakano T, Takahashi M, Nagao A. 2005. Orally administered crocetin and crocins are absorbed into blood plasma as crocetin and its glucuronide conjugates in mice. *J Agric Food Chem*, 53: 7302-7306.

Bhosale P, Serban B, Bernstein P S. 2009. Retinal carotenoids can attenuate formation of A2E in the retinal pigment epithelium. *Arch Biochem Biophys*, 483: 175-181.

Bisti S, Maccarone R, Falsini B. 2014. Saffron and retina: neuroprotection and pharmaco-kinetics. *Visual Neurosci*, 1-7. doi:10.1017/S0952523814000108.

Chábera P, Fuciman M, Hříbek P, Polívka T. 2009. Effect of carotenoid structure on excited-state dynamics of carbonyl carotenoids. *Phys Chem Chem Phys*, 11: 8795-8803.

Elliott J G, Williams N S. 2012. Nutrients in the battle against age-related eye diseases. *American Optometric Association*. doi: 10.1016/j.optm.2011.11.006

Falsini B, Piccardi M, Minnella A, Savastano C, Capoluongo E, Fadda A, Balestratti E, Maccarone R, Bisti S. 2010. Influence of saffron supplementation on retinal flicker sensitivity in early age-related macular degeneration. *Invest Ophthalmol Vis Sci*, 51: 6118-6124.

Fernández-Sánchez L, Lax P, Esquiva G, Martín-Nieto J, Pinilla I, Cuenca N. 2012. Safranal, a saffron constituent, attenuates retinal degeneration in P23H rats. *PLoS ONE*, 7(8): e43074.

Fontaine V, Lafont R, Sahel J A, Veillet S. 2011. Utilisation de composes et composition pour le traitement de la dégénérescence maculaire liée à l'âge (DMLA) [Use of compounds and composition for the treatment of age-related macular degeneration (ARMD)]. Application FR 25506 (filed on May 14, 2011).

Goralczyk R, Buser S, Bausch J, Bee W, Zühlke U, Barker F M. 1997. Occurrence of birefringent retinal inclusions in cynomolgus monkeys after high doses of canthaxanthin. *Invest Ophthalmol Vis Sci*, 38: 741-752.

Hagiwara A, Imai N, Ichihara T, Sano M, Tamano S, Aoki H, Yasuhara K, Koda T, Nakamura M, Shirai T. 2003. A thirteen-week oral toxicity study of annatto extract (norbixin), a natural food color extracted from the seed of annatto (Bixaorellana L.), in Sprague-Dawley rats. *Food Chem Toxicol*, 41: 1157-1164.

Laabich A, Vissvesvaran G P, Lieu K L, Murata K, McGinn T E, Manmoto C C, Sinclair J R, Karliga I, Leung D W, Fawzi A, Kubota R. 2006. Protective effect of crocin against blue light- and white light-mediated photoreceptor cell death in bovine and primate retinal primary cell culture. *Invest Ophthalmol Vis Sci*, 47: 3156-3163.

Lévy L W, Regalado E, Navarette S, Watkins R H. 1997. Bixin and norbixin in human plasma: Determination and study of the absorption of a single dose of annatto food color. *Analyst*, 122: 977-980.

Liu X, Osawa T. 2007. Cisastaxanthin and especially 9-cisastaxanthin exhibits a higher antioxidant activity in vitro compared to the all-trans isomer. *Biochem Biophys Res Comm*, 357: 187-193.

Maccarone R, Di Marco S, Bisli S. 2008. Saffron supplementation maintains morphology and function after exposure to damaging light in mammalian retina. *Invest Ophthalmol Vis Sci*, 49: 1254-1261.

Maeda T, Maeda A, Golczak M, Palczewski K. 2008. Retinopathy in mice induced by disrupted all-trans-retinal clearance. *J Biol Chem*, 283: 26684-26693.

Maeda T, Maeda A, Matosky M, Okano K, Roos S, Tang J, Palczewski K. 2009. Evaluation of potential therapies for a mouse model of human age-related macular degeneration caused by delayed all-trans-retinal clearance. *Invest Ophthalmol Vis Sci*, 50: 4917-1925.

Melendez-Martinez A J, Stinco C M, Liu C, Wang X D. 2013. A simple HPLC method for the comprehensive analysis of cis/trans (Z/E) geometrical isomers of carotenoids for nutritional studies. *Food Chem*, 138: 1341-1350.

Montenegro M A, De O Rios A, Mercadante A Z, Nazareno M A, Borsarelli C D. 2004. Model studies on the photosensitized isomerization of bixin. *J Agric Food Chem*, 52: 367-373.

Parisi V, Tedeschi M, Gallinaro G, Varano M, Saviano S, Piermarocchi S. 2008. Carotenoids and antioxidants in age-related maculopathy Italian study: multifocal electroretinogram modifications after 1 year. *Ophthalmology*, 115(2): 324-333.

Phan-Thi H, Waché Y. Isomerization and increase in the antioxidant properties of lycopene from Momordicacochinensis (gac) by moderate heat treatment with UV-Vis spectra as a marker. *Food Chem*, 156: 58-63.

Pinazo-Duran M D, Gómez-Ulla F, Arias L, Araiz J, Casaroli-Marano R, Gallego-Pinazo R, Garcia-Medina J J, López-Gálvez M A, Manzanaq L, Salas A, Zapara M, Diaz-Llopis M, Garcia-Layana A. 2014. Do nutritional supplements have a role in age macular degeneration prevention? *J Ophthalmology*, article ID 901686.

Pintea A, Rugina D O, Pop R, Bunea A, Socaciu C. 2011. Xanthophylls protect against induced oxidation in cultured human retinal pigment epithelial cells. *J Food Compos Anal*, 24(6): 830-836.

Rios A D O, Borsarelli C D, Mercadante A Z. 2005. Thermal degradation kinetics of bixin in an aqueous model system. *J Agric Food Chem*, 53: 2307-2311.

Sparrow J R, Cai B. 2001. Blue light-induced apoptosis of A2E-containing RPE: involvement of caspase-3 and protection by Bcl-2. *Invest Ophthalmol Vis Sci*, 42:1356-1362.

Subczynski W K, Wisniewska A, Widomska J. 2010. Location of macular pigments in the most vulnerable regions of photoreceptor outer-segment membranes. *Arch Biochem Biophys*, 504: 61-66.

Tsuruma K, Shimazaki H, Nakashima K, Yamauchi M, Sugitani S, Shimazawa M, Iinuma M, Hara H. 2012. Annatto prevents retinal degeneration induced by endoplasmic reticulum stress in vitro and in vivo. *Mol Nutr Food Res*, 56: 713-724.

Veillet S, Lafont R, Dioh W. 2009. Cosmetic composition for protection from the sun containing urucum extract. Priority Application FR2009-54354 A (Jun. 25, 2009), Application No. FR 2009-54354, WO 2010-FR51323.

Verma R S, Middha D. 2010. Analysis of saffron (*Crocus sativus* L.) stigma components by LC-MS-MS. *Chromatographia*, 71: 117-123.

Widomska J, Subczynski W K. 2014. Why has nature chosen lutein and zeaxanthin to protect the retina? *J Clin Exp Ophthalmol*, 5(1): 326, doi:10:4172/2155-9570.1000326.

Wu L, Ueda K, Nagasaki T, Sparrow J T. 2014. Light damage in Abca4 and Rpe65$^{rd12}$ mice. *Invest Ophthalmol Vis Sci*, 55: 1910-1918.

Yamauchi M, Tsuruma K, Imai S, Nakanishi T, Umigai N, Shimazawa M, Hara H. 2011. Crocetin prevents retinal degeneration induced by oxidative stress and endoplasmic reticulum stress via inhibition of caspase activity. *Mol Cell Pharmacol*, 650: 110-119.

Young J P, Zhou J, Nakanishi K, Sparrow J N. 2005. Anthocyanins protect against A2E photooxidation and membrane permeabilization in retinal pigment epithelial cells. *Photochem Photobiol*, 81: 529-536.

The invention claimed is:

1. A method of photoprotecting cells of a retinal pigment epithelium (RPE) in mammals comprising administering to a mammal a composition comprising norbixin obtained by purification from an extract of *Bixa orellana* seeds, per day, in an amount of between 0.48 mg/kg of body weight and 48 mg/kg of body weight.

2. The method as claimed in claim 1, wherein the composition comprises more than 95% by weight of norbixin.

3. The method as claimed in claim 1, wherein the composition comprises more than 90% by weight of norbixin in its 9'-cis form of formula (I):

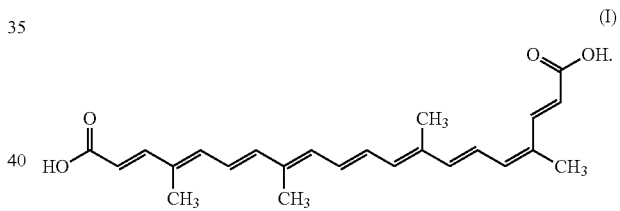

4. The method as claimed in claim 1, wherein the composition comprises at least one element chosen from zinc, vitamin C and vitamin E.

5. The method as claimed in claim 1, wherein the composition is in the form of a food supplement or of a medicament.

6. The method as claimed in claim 1, wherein the composition comprises a support acceptable for being ingested, injected in the eye, injected systemically or injected into the blood.

7. The method as claimed in claim 1, wherein the composition is administered to prevent damage to a retina caused by exposure to a blue radiation corresponding to a blue band of a visible light spectrum, having a wavelength of between 435 nm and 490 nm.

8. The method as claimed in claim 1, wherein the composition is administered to treat age-related macular degeneration (ARMD) in mammals.

9. The method as claimed in claim 1, wherein the composition is administered to treat at least one of Stargardt disease and retinitis pigmentosa in mammals.

10. The method as claimed in claim 2, comprising more than 90% by weight of norbixin in its 9'-cis form of formula (I):

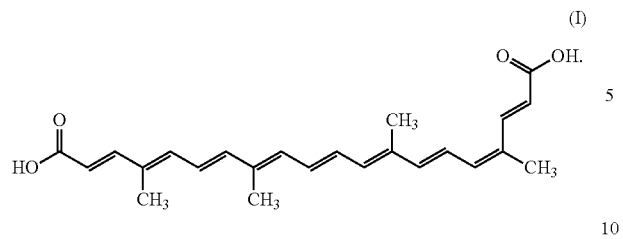
11. The method as claimed in claim 1, wherein the administered amount of the composition to the mammal, per day, is between 0.6 mg/kg of body weight and 20 mg/kg of body weight.